United States Patent [19]

Schickaneder et al.

[11] Patent Number: 4,921,856
[45] Date of Patent: May 1, 1990

[54] DIHYDROPYRIDAZINONE DERIVATIVES, A PROCESS FOR THEIR PREPARATION AND PHARMACEUTICAL PREPARATIONS CONTAINING THESE COMPOUNDS

[75] Inventors: Helmut Schickaneder, Eckental; Peter Mörsdorf, Langenzenn; Volker Pfahlert, Nuremberg; Heidrun Engler, Cadolzburg; Kurt H. Ahrens, Nuremberg, all of Fed. Rep. of Germany

[73] Assignee: Heumann Pharma GmbH & Company, Nuremberg, Fed. Rep. of Germany

[21] Appl. No.: 176,689

[22] Filed: Apr. 1, 1988

[30] Foreign Application Priority Data

Aug. 26, 1987 [DE] Fed. Rep. of Germany ....... 3728491

[51] Int. Cl.$^5$ .................... C07D 237/04; A61K 31/50
[52] U.S. Cl. .................................... 514/252; 544/238; 549/239
[58] Field of Search ................. 544/238, 239; 514/252

[56] References Cited

U.S. PATENT DOCUMENTS 4,639,451 11/1987 Katakami et al. ................. 544/238
4,661,484 4/1987 Okushima et al. ................. 544/238

FOREIGN PATENT DOCUMENTS 0178189 4/1986 European Pat. Off. .
2157453 5/1973 Fed. Rep. of Germany .

OTHER PUBLICATIONS

Chem. Abstract, 90:168635t, (1979).
Chem. Abstract, 101:90957y (1984).
Chem. Abstract, 97:55827h (1982).
Chem. Abstract, 107:23352h (1987).
Chem. Abstract, 100:51594n (1984).

*Primary Examiner*—Nicholas S. Rizzo
*Attorney, Agent, or Firm*—Burns, Doane, Swecker & Mathis

[57] ABSTRACT

New dihydropryidazinone derivatives corresponding to the following formula

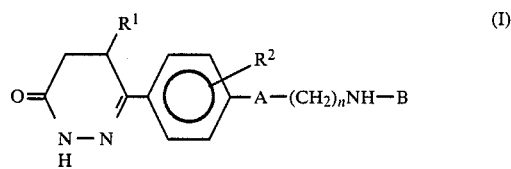

and a process for their preparation and pharmaceutical preparations containing these compounds are described. These compounds are effective positively inotropic substances with an improved therapeutic profile.

13 Claims, No Drawings

DIHYDROPYRIDAZINONE DERIVATIVES, A PROCESS FOR THEIR PREPARATION AND PHARMACEUTICAL PREPARATIONS CONTAINING THESE COMPOUNDS

BACKGROUND OF THE INVENTION

Cardiac glycosides such as digoxin and digitoxin and sympathomimetic drugs are traditionally used for the treatment of congestive cardiomyopathy and cardiac insufficiency. The cardiac glycosides have, however, distinct toxic side effects and only a narrow therapeutic range while the sympathomimetic drugs show undesirable chronotropic and arrythmogenic side effects and are ineffective when taken orally.

This situation has led in recent years to the development of new, positively inotropic substances, of which amrinone (J. R. Benotti et al., N. Engl. J. Med. 299, 1373 (1978) and milrinone (A. A. Alousi et al., J. Cardiovasc. Pharmacol 5, 792 (1983) are examples.

These substances, however, have an undesirable spectrum of side effects when administered orally so that their use has been restricted to other forms of administration.

It was therefore an object of the present invention to provide new, more effective positively inotropic substances with an improved therapeutic profile.

This problem is solved by the present invention.

SUMMARY OF THE INVENTION

The invention relates to dihydropyridazinone derivatives corresponding to the formula I

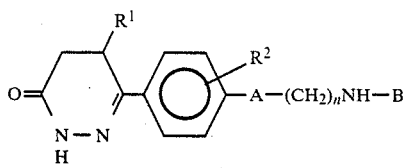

wherein $R^1$ denotes a hydrogen atom or a straight chained or branched $C_1$ to $C_4$ alkyl group, $R^2$ denotes a hydrogen atom, a straight chained or branched $C_1$ to $C_4$ alkyl group, a $C_1$ to $C_4$ alkoxy group, a halogen atom, a nitro group or an amino group, A denotes an oxygen atom, the group NH or

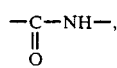

an imidazole ring attached in positions 1 to 4 or a single bond, and B denotes a hydrogen atom or a group of the formula

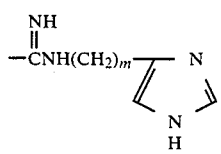

wherein m has the value 2 or 3 and n stands for an integer with a value from 0 to 6, and to the physiologically acceptable salts thereof.

DESCRIPTION OF THE PREFERRED EMBODIMENT

In the formula I, $R^1$ denotes a hydrogen atom or a straight chained or branched $C_1$ to $C_4$ alkyl group. The methyl, ethyl and n-propyl group are examples of such straight chained or branched $C_1$ to $C_4$ alkyl groups, the methyl group being preferred. $R^2$ stands for a hydrogen atom, a straight chained or branched $C_1$ to $C_4$ alkyl group as defined above with reference to $R^1$, a $C_1$ to $C_4$ alkoxy group, for example a methoxy or ethoxy group, a halogen atom, for example a fluorine, chlorine or bromine atom, a nitro group or an amino group.

The symbol A stands for an oxygen atom, the group NH or

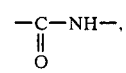

an imidazole ring attached through positions 1 and 4, or a single bond. The group

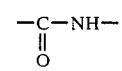

may be attached to the phenyl ring either through the carbonyl group or through the nitrogen atom, the linkage through the carbonyl group being preferred. The imidazole ring is preferably attached to the phenyl ring through the nitrogen atom in position 1. The alkylene group denoted by $-(CH_2)_n-$ is attached through the 4 position.

In the formula I, the symbol B stands for a hydrogen atom or a group of the formula

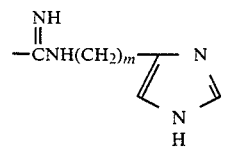

wherein m has the value 2 or 3, preferably 3, and n stands for an integer with a value from 0 to 6.

A preferred group of compounds according to the present invention is characterised in that in the general formula I, $R^1$ stands for a hydrogen atom or a straight chained or branched $C_1$ to $C_4$ alkyl group, $R^2$ stands for a hydrogen atom, a straight chained or branched $C_1$ to $C_4$ alkyl group, a $C_1$ to $C_4$ alkoxy group, a halogen atom, a nitro group or an amino group, A stands for an oxygen atom, the group NH or

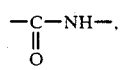

an imidazole ring attached in positions 1 or 4 or a single bond, B denotes a hydrogen atom and n stands for an integer with a value from 0 to 6.

Another preferred group of compounds according to the present invention is characterised in that in the general formula I, $R^1$ denotes a hydrogen atom or a straight chained or branched $C_1$ to $C_4$ alkyl group, $R^2$ denotes a hydrogen atom or a straight chained or branched $C_1$ to $C_4$ alkyl group, a $C_1$ to $C_4$ alkoxy group, a halogen atom, a nitro group or an amino group, A denotes an oxygen atom, the group NH or $$-\underset{\underset{O}{\|}}{C}-NH-,$$

an imidazole ring attached in positions 1 and 4 or a single bond, B denotes a group of the formula $$-\underset{\underset{}{\|}}{\overset{NH}{C}}NH(CH_2)_m-\underset{\underset{H}{}}{\overset{}{\diagdown}}\overset{N}{\underset{N}{\diagup}}$$

wherein m has the value 2 or 3, and n denotes an integer with a value from 0 to 6.

Another preferred group of compounds according to the present invention is characterised in that $R^1$ in the general formula I stands for a straight chained or branched $C_1$ to $C_4$ alkyl group, in particular a methyl group, $R^2$ stands for a hydrogen atom, A stands for an oxygen atom, the group NH or $$-\underset{\underset{O}{\|}}{C}-NH-.$$

an imidazole ring attached in positions 1 and 4 or a single bond, B stands for a hydrogen atom and n stands for an integer with a value from 0 to 6.

Lastly, yet another preferred group of compounds according to the present invention is characterized in that in the general formula I, $R^1$ denotes a hydrogen atom or a straight chained or branched $C_1$ to $C_4$ alkyl group, in particular a methyl group, and $R^2$ denotes a hydrogen atom, A denotes an oxygen atom, the group NH or $$-\underset{\underset{O}{\|}}{C}-NH-,$$

an imidazole ring attached in positions 1 and 4, or a single bond, B denotes a group of the formula $$-\underset{\underset{}{\|}}{\overset{NH}{C}}NH(CH_2)_m-\underset{\underset{H}{}}{\overset{}{\diagdown}}\overset{N}{\underset{N}{\diagup}}$$

wherein m has the value 2 or 3, in particular 3, and n stands for an integer with a value from 0 to 6.

The present invention further relates to a process for the preparation of the compounds described above, characterised in that (a) for the preparation of compounds corresponding to the general formula I in which $R^1$, $R^2$, A and n have the meanings defined above and B stands for a hydrogen atom, ($a_1$) the phthalimide group is split off from a phthalimide compound corresponding to the formula II $$(II)$$

wherein $R^1$, and $R^2$, A and n have the meanings indicated above by a reaction with hydrazine or a chemical equivalent thereof, an aliphatic primary amine or an acid, and the phthalimide compound is thereby converted into a compound corresponding to the formula I, or ($a_2$) a compound corresponding to the formula III $$(III)$$

wherein $R^1$, $R^2$, A and n have the meanings indicated above and $R^3$ stands for an optionally substituted $C_1$ to $C_4$ alkyl group or a hydrogen atom, is reacted with hydrazine or a chemical equivalent thereof with ring closure to form the pyridazinone ring and hydrazinolysis of the phthalimide protective group to produce a compound corresponding to the formula I, or (b) for the preparation of compounds corresponding to the formula I in which $R^1$, $R^2$, A and n have the meanings defined above and B stands for a group of the formula $$-\underset{\underset{NH}{\|}}{C}-NH-(CH_2)_m-\underset{\underset{H}{}}{\overset{}{\diagdown}}\overset{N}{\underset{N}{\diagup}}$$

wherein m has the value 2 or 3, ($b_1$) a compound corresponding to the formula IV $$(IV)$$

wherein $R^1$, $R^2$, A and n have the meanings defined above, $R^4$ stands for an optionally substituted $C_1$ to $C_4$ alkyl group and X denotes a halogen atom or the group $-OSO_2OR^4$ is reacted with a m-(imidazol-4-yl) alkylamine corresponding to the formula V $$(V)$$

wherein m has the value 2 or 3 to form a compound corresponding to the formula I, or (b₂) a compound corresponding to the formula VI

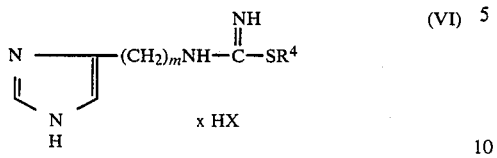

wherein m, $R^4$ and X have the meanings defined above is reacted with a compound corresponding to the formula Ia

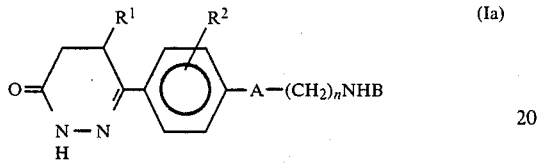

wherein $R^1$, $R^2$, A and n have the meanings indicated above and B stands for a hydrogen atom, to form a compound corresponding to the formula I and in that the compound obtained according to (a₁) to (a₂) or (b₁) to (b₂) is optionally converted into a physiologically acceptable salt thereof in known manner.

Compounds according to the invention corresponding to the formula I in which $R^1$, $R^2$, A and n have the meanings defined above and B stands for a hydrogen atom may thus be prepared by two different variations of the process, namely (a₁) by the reaction of a compound corresponding to the formula II

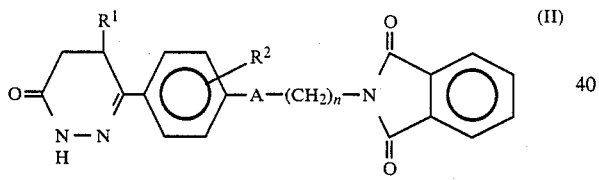

wherein $R^1$, $R^2$, A and n have the meanings indicated above, with hydrazine or a chemical equivalent thereof or an aliphatic primary amine, for example methylamine, or an acid. Chemical equivalents of hydrazine are in particular hydrazine hydrate, hydrazine ethanolate and similar solvates or salts thereof. Hydrazine is preferably used in the form of hydrazine hydrate. The reaction with hydrazine or its equivalents and amines is preferably carried out with an excess of reactant and in a polar solvent, for example an alcohol such as methanol, ethanol and isopropanol. The reaction is carried out at temperatures from room temperature to the boiling point of the solvent used, preferably at the reflux temperature. When amines are used, the reaction may be carried out at an elevated pressure. Acid hydrolysis of the compounds corresponding to the formula II is carried out in an aqueous mineral acid such as hydrochloric, hydrobromic or hydriodic acid, sulphuric acid or phosphoric acid or in a dilute organic acid such as acetic acid or in mixtures of aqueous mineral acids and organic acids at elevated temperatures, for example at the reflux temperature. In this reaction, the phthalimide group is split off from the compound corresponding to the formula II to yield the compound corresponding to the formula I.

The other possible variation consists of (a₂) the reaction of a compound corresponding to the formula III

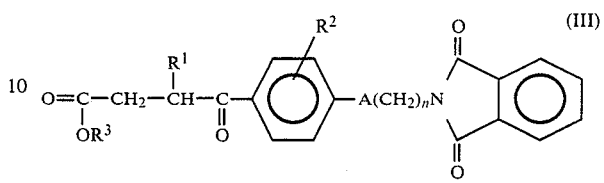

wherein $R^1$, $R^2$, A and n have the meanings defined above and $R^3$ denotes an optionally substituted $C_1$ to $C_4$ alkyl group, for example a methyl or ethyl group which may be substituted, for example with a halogen atom as defined above, with a $C_1$ to $C_4$ alkyl group as defined above or with a $C_1$ to $C_4$ alkoxy group as defined above, or it denotes a hydrogen atom, with hydrazine or its chemical equivalent as defined in the description of process variation (a₁). The reaction preferably takes place with an excess of hydrazine or its chemical equivalent, as in process variation (a₁) and the hydrazine is again preferably in the form of hydrazine hydrate. The reaction is again carried out in a polar solvent, for example an alcohol such as methanol, ethanol, isopropanol or n-butanol. The reaction is carried out at an elevated temperature, preferably at the reflux temperature of the solvent used, and optionally with an acid catalyst, for example acetic acid. The reaction is accompanied by ring closure to form the pyridazione ring and hydrazinolysis of the phthalimide protective group to result in a compound corresponding to the formula I.

Compounds according to the invention corresponding to the formula I in which $R^1$, $R^2$, A and n have the meanings defined above and B stands for a group of the formula

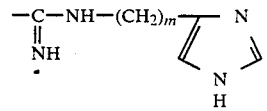

are prepared by one of the following process variations:

(b₁) by the reaction of an isothiuronium salt corresponding to the formula IV

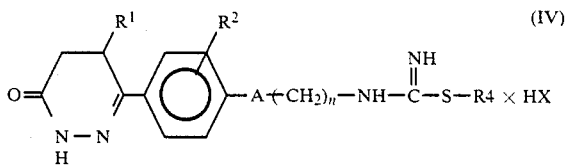

wherein $R^1$, $R^2$, A and n have the meanings defined above, $R^4$ denotes a $C_1$ to $C_4$ alkyl group, for example a methyl or ethyl group which may be substituted, for example by a halogen atom as defined above, and X stands for a halogen atom, for example a fluorine, chlorine or bromine atom, or for the group —OSO₂OR⁴ with a m-(imidazol-4-yl) alkylamine corresponding to the general formula V

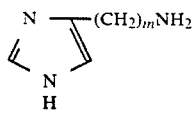

(V)

wherein m has the value 2 or 3. The compounds are reacted together in equimolar quantities in a polar solvent such as pyridine, acetonitrile or an alcohol such as ethanol, isopropanol or n-butanol at temperatures from room temperature up to the reflux temperature of the solvent used, preferably at the reflux temperature; ($b_2$) by the reaction of a compound corresponding to the formula VI.

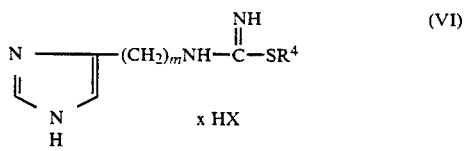

(VI)

wherein $R^4$, m and X have the meanings indicated above with an amine corresponding to the general formula Ia

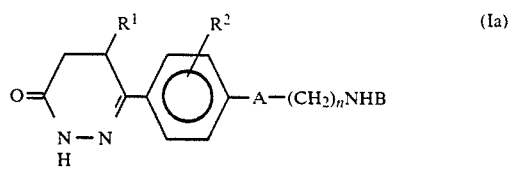

(Ia)

wherein $R^1$, $R^2$, A and n have the meanings defined above and B stands for a hydrogen atom.

Concerning the solvents used, the reaction temperature and the stoichiometric proportions of the reactants, the same applies to these reactions as has already been stated with reference to process variation ($b_1$).

The compounds according to the invention obtained by the various process variations are isolated and purified by the usual methods, for example by crystallization from suitable solvents, chromatographic procedures, etc.

The compounds according to the invention corresponding to the formula I may be present both in several stereoisomeric forms and in several tautomeric forms. The invention therefore covers all stereoisomeric and tautomeric forms as well as the hydrates of the compounds corresponding to the formula I.

The compounds obtained by the individual variations of the process are optionally converted into their physiologically acceptable salts. These salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenyl acetic acid, tartaric acid, citric acid, fumaric acid, methane sulphonic acid, embonic acid, etc.

The compounds according to the invention may be formulated as desired for administration. This invention therefore also extends to pharmaceutical preparations containing at least one compound according to the invention for use in human or veterinary medicine. Such pharmaceutical preparations may conventionally be prepared with the aid of one or more pharmaceutical carriers or diluents.

The compounds according to the invention may therefore be formulated for oral, buccal, topical, parenteral or rectal administration.

For oral administration, the pharmaceutical preparation may be presented, for example, in the form of tablets, capsules, powders, solutions, syrups or suspensions, all of which may be prepared by the conventional methods using acceptable diluents.

For buccal administration, the pharmaceutical preparation may be in the form of tablets or sachets formulated in the usual manner.

For parenteral administration, the compounds according to the invention may be formulated as preparations for bolus injection or for continuous infusion. Formulations for injection may be in the form of single dose ampoules or multiple dose containers with added preservative.

The pharmaceutical preparations may be in the form of suspensions, solutions or emulsions in oily or aqueous carriers and they may contain formulating auxiliaries such as dispersing or suspending agents and/or stabilizers.

Alternatively, the active ingredient may be prepared in powder form to be reconstituted with a suitable carrier such as sterile, pyrogen free water before use.

The compounds according to the invention may also be formulated for rectal administration, for example as suppositories or retention enemas which may, for example, contain the usual suppository excipients such as cocoa butter or other glycerides.

For topical application, the compounds according to the invention may be formulated as ointments, creams, gels, lotions, powders or sprays in the usual manner.

For oral administration, a suitable daily dose of compounds according to the invention is composed of one to four doses with a total of 5 mg to 1 g per day, depending on the patient's condition. In some cases it may be necessary to deviate from these quantities, depending on the individual response to the active ingredient, the nature of its formulation and the time or time interval at which administration takes place. Thus there are cases in which it may be sufficient to use less than the minimum quantity indicated above whereas in other cases it may be necessary to exceed the upper limit.

The following pharmacological data demonstrate the activity data of the compounds according to the invention obtained in various screening tests.

1. Determination of the positive inotropic action on isolated, electrically stimulated guinea pig's papillary muscle.

(a) Method

Electrically stimulated papillary muscle preparations from the right ventricle of guinea pigs were used for the investigations. The animals weighed from 300 to 500 g. They were killed by a blow to the back of the neck and drained of blood. The heart was rapidly removed and further preparation was carried out in a Krebs solution at room temperature. The isolated preparations were then fixed to plexiglass holders with stimulating electrodes and introduced into baths of 100 ml capacity. The preparations were gassed with carbogen (95% $O_2$ + 5% $CO_2$) at an experimental temperature of 31° C.

The contractions were registered by means of electromechanical converters (Statham UC 2) and recorded on direct recorders by way of direct voltage measuring bridges (H. Sachs-Elektronik). The signals were at the same time evaluated electronically and expressed digitally (DIO-1, Mikro-mess). Measurements were carried out whenever a steady state had developed.

The initial tension in the papillary muscle was 0.5 g. The stimulating frequency was 1 Hz and the duration of the rectangular pulses was 3 ms. Stimulation was carried out with currents at above threshold intensities.

(b) Measured values

| Example No. | Max. Contraction Force Increase in % | $pD_2$ Value |
| --- | --- | --- |
| 1 | +18% | 5.6 |
| 2 | +81% | 5.3 |
| 3 | +31% | 6.8 |
| 6 | +48% | 5.2 |
| 7 | +51% | 4.9 |
| 8 | +43% | 6.2 |
| 9 | +66% | 6.2 |
| Amrinone (Comparison) | +34% | 5.8 |

2. Investigations on Isolated Perfused Langendorff Hearts (Guinea Pigs).

(a) Method

To determine the haemodynamic effects of the compounds according to the invention on isolated, perfused guinea pig hearts, the arrangement of Langendorff was modified according to P. R. Beckett (J. Pharm. Pharmacol 22, 818 (1970)) and R. M. Abel and R. L. Reis (Circ. Res. 27, 961 (1970)). The spontaneously beating guinea pig hearts were catheterised in the left ventricle and perfused with solutions of test substances in physiological saline solution/ethanol (9:1) at concentrations of $10^{-5}$ and $10^{-6}$ mol/l at a constant perfusion pressure of 60 mm Hg.

(b) Measured Values

| Example No. | Conc. (Mol/l) | Percentage Changes Compared with Controls | | |
| --- | --- | --- | --- | --- |
| | | Contractility dp/dt | Coronary Flow | Heart rate |
| 2 | $10^{-6}$ | +46% | +25% | +9% |
| 3 | $10^{-5}$ | +73% | +5% | +5% |
| 6 | $10^{-5}$ | +163% | +129% | +15% |
| 7 | $10^{-6}$ | +190% | +23% | +25% |
| 8 | $10^{-6}$ | +130% | +52% | +23% |
| Amrinone (Comparison) | $10^{-5}$ | +25% | +46% | +18% |

EXAMPLE 1

6-[4-[4-(3-aminopropyl)-1H-imidazol-1-yl]phenyl]-4,5-dihydro-3(2H)-pyridazinone dihydrochloride

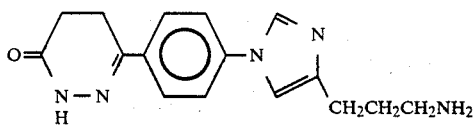

(a)
3-[4-[4-(3-phthalimidopropyl)-1H-imidazol-1-yl]benzoyl]-propionic acid 5.10 g (20 mmol) of 4-(3-phthalimidopropyl)-imidazole followed by 3.92 g (20 mmol) of 3-(4-fluorobenzoyl)-propionic acid are added portionwise to a suspension of 1.20 g (40 mmol) of sodium hydride (80% on paraffin oil) in 50 ml of dimethyl sulphoxide. The reaction mixture is initially stirred at room temperature until gas evolution ceases and then at 100° C. for 17 hours. After cooling, the mixture is poured out on 50 ml of water and extracted with 3×50 ml dichloromethane. The aqueous phase is then adjusted to pH 5 with 2N hydrochloric acid and the precipitated solid is suction filtered and recrystallized from methanol.

Yield: 4.92 g (57%).
M.pt. 200°–203° C.
$C_{24}H_{21}N_3O_5$ (431.45).

(b)
6-[4-[4-(3-aminopropyl)-1H-imidazol-1-yl]phenyl]-4,5-dihydro-3(2H)-pyridazinone dihydrochloride.

3.02 g (7 mmol) of 3-[4-[4-(3-phthalimidopropyl)-1H-imidazol-1-yl]benzoyl]-propionic acid and 1.7 ml (35 mmol) of hydrazine hydrate are boiled in 30 ml of ethanol for 6 hours. After cooling to room temperature, the solid obtained is suction filtered and the mother liquor is completely concentrated by evaporation under vacuum. The residue is taken up with 10 ml of ethanol, and 2 ml of isopropanolic hydrochloric acid (∼10 Mol/l) are added thereto. The precipitated solid is suction filtered, washed with methanol and dried under vacuum.

Yield: 1.22 g (47%).
M.pt. 235°–238° C. (decomp.).
$C_{16}H_{21}Cl_2N_5O$ (370.28).
$^1$H-NMR data (D$_2$O, TMSP as internal standard): δ=2.2 (quin) 2H, 2.6 (t) 2H, 2.9–3.4 (m) 6H, 7.7–8.1 (m) 5H, 9.15 (d) 1H ppm.

EXAMPLE 2

6-[4-[4-(3-aminopropyl)-1H-imidazol-1-yl]phenyl]-4,5-dihydro-5-methyl-3(2H)-pyridazinone dihydrochloride

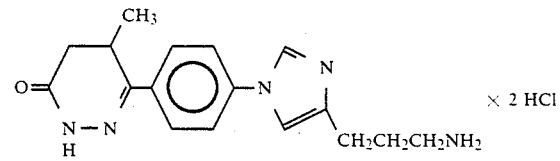

(a)
3-[4-[4-(3-phthalimidopropyl)-1H-imidazol-1-yl]benzoyl]-butyric acid

Prepared by a method analogous to that of Example (a) from 2.6 g (10.2 mmol) of 4-(3-phthalimidopropyl)-imidazole and 2.2 g (10.5 mmol) of 3-(4-fluorobenzoyl)-butyric acid. 3.4 g (75%) of a brownish, viscous oil is obtained which is used without further purification for the next stage.

$C_{25}H_{23}N_3O_5$ (445.50)

(b)
6-[4-[4-(3-aminopropyl)-1H-imidazol-1-yl]phenyl]-4,5-dihydro-5-methyl-3(2H)-pyridazinone dihydrochloride 2.3 g (5.2 mmol) of 3-[4-[4-(3-pthalimidopropyl)-1H-imidazol-1-yl]benzoyl]-butyric acid and 1.25 ml (25.5 mmol) of hydrazine hydrate are boiled in 20 ml of ethanol. After 6 hours, the reaction mixture is cooled, the resulting solid is suction filtered and the filtrate is completely evaporated under vacuum. The residue is dissolved in 10 ml of ethanol and 1.5 ml of isopropanolic hydrochloric acid is then added with stirring. When stirring is continued at room temperature, a colourless solid crystallizes. This is suction filtered, washed with ethanol and dried under vacuum.

Yield: 1.03 g (52%).
M.pt. 175° C.
$C_{17}H_{22}Cl_2N_5O$ (383.30).
$^1$H-NMR data (D$_2$O, TMSP as internal standard):
δ=1.1 (d) 3 H, 2.2 (quin) 2 H, 2.5–3.0 (m) 4 H, 3.1–3.6 (m) 3 H, 7.6–8.0 (m) 5 H, 8.7 (d) 1 H ppm.

EXAMPLE 3

6-[4-(3-aminopropylamino)phenyl]-4,5-dihydro-5-methyl-3(2H)-pyridazinone

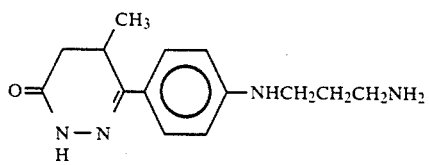

(a)
3-[4-[N-(3-phthalimidopropyl)acetamido]benzoyl]-butyric acid 30.0 g (120 mmol) of 3-(4-acetamidobenzoyl)-butyric acid are added to a suspension of 7.6 g (253 mmol) of sodium hydride (80%) in 150 ml of dimethyl sulphoxide and the mixture is stirred for 30 minutes at 60° C. After the addition of 33.2 g (120 mmol) of N-(3-bromopropyl)-phthalimide, stirring is continued at 80° C. for 6 hours. After cooling, the reaction mixture is poured out on 200 ml of iced water and extracted with 3×100 ml of dichloromethane. The extracts are discarded. The aqueous phase is then adjusted to pH 6.5 with 2N hydrochloric acid and again extracted with 3×100 ml of dichloromethane. The combined organic phases are dried and concentrated by evaporation under vacuum. The oil obtained as residue crystallizes when triturated with 20 ml of ethanol.

Yield: 23.1 g (44%).
$C_{24}H_{24}N_2O_6$ (436.46).

(b)
6-[4-[N-(3-aminopropyl)acetamido]phenyl]-4,5-dihydro-5-methyl-3(2H)-pyridazinone hydrochloride.

4.7 g (10.8 mmol) of 3-[4-[N-(3-phthalimidopropyl)acetamido]-benzoyl]-butyric acid and 2.7 ml (55 mmol) of hydrazine hydrate are boiled under reflux in 60 ml of ethanol for 1 hour. The filtrate obtained after suction filtration of the precipitated solid is evaporated under vacuum and the residue is taken up with 20 ml of 2N hydrochloric acid. After refiltration, the mother liquor is evaporated under vacuum. 2.82 g (80%) of an orange yellow, viscous oil is obtained as residue which is used for further reactions without purification.
$C_{16}H_{23}ClN_4O_2$ (33.84).

(c)
6-[4-(3-aminopropylamino)phenyl]-4,5-dihydro-5-methyl-3(2H)-pyridazinone 2.8 g (8.3 mmol) of 6-[4-[N-(3-aminopropyl)acetamido]phenyl]-4,5-dihydro-5-methyl-3(2H)-pyridazinone hydrochloride are boiled under reflux in 30 ml of 2N hydrochloric acid for 2 hours. The solution is concentrated by evaporation under vacuum and the residue is taken up with 20 ml of saturated potassium carbonate. After this residue has been extracted twice with 30 ml portions of isopropanol, the combined organic phases are dried over potassium carbonate and concentrated by evaporation under vacuum. The residue is chromatographically purified with ethyl acetate/ethanol/conc. ammonia (15:10:2) on silica gel.

Yield: 1.2 g (56%).
Colourless solid, m.pt. 68°–70° C.
$C_{14}H_{20}N_4O$ (260.34).
$^1$H-NMR data (CD$_3$OD, TMS as internal standard):
δ=1.1 (d) 3 H, 1.7 (quin) 2 H, 2.2–2.9 (m) 4 H, 3.1–3.5 (m) 3 H, 4.9 (broad) 4 H replaceable by D$_2$O, 6.7 (d) 2 H, 7.7 (d) 2 H ppm.

EXAMPLE 4

6-[4-(3-aminopropoxy)phenyl]-4,5-dihydro-5-methyl-3(2H)-pyridazinone

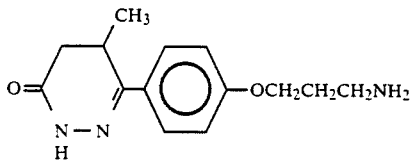

(a) 3-[4-(3-phthalimidopropoxy)benzoyl]-butyric acid methyl ester.

26.0 g (200 mmol) of anhydrous aluminum chloride are suspended in 200 ml of 1,2-dichloroethane and cooled to 10° C. 8.2 g (50 mmol) of 3-methoxycarbonyl-2-methyl-propionic acid chloride in 20 ml of 1,2-dichloroethane followed by 14.0 g (50 mmol) of (3-phthalimidopropyl)-phenyl ether in 50 ml of 1,2-dichloroethane are added dropwise with further cooling at such a rate that the reaction temperature does not rise above 10° C.

After further stirring for 18 hours at room temperature, the mixture is poured out on 400 ml of ice water. After phase separation, the aqueous phase is extracted twice with 100 ml portions of dichloromethane. The combined organic phases are dehydrated with sodium sulphate, filtered and concentrated by evaporation under vacuum. 20.9 g (quant.) of an orange yellow oil are obtained. This oil solidifies in an ice bath after the addition of 50 ml of ethanol. The product is used for further reactions without purification.
$C_{23}H_{23}NO_6$ (409.44).

(b)
6-[4-(3-aminopropoxy)phenyl]-4,5-dihydro-5-methyl-3(2H-pyridazinone.

12 ml (250 mmol) of hydrazine hydrate and 0.1 ml of glacial acetic acid are added to 20.5 g (50 mmol) of 3-[4-(3-phthalimidopropoxy)benzoyl]-butyric acid methyl ester in 120 ml of ethanol and the reaction mixture is boiled under reflux for 1.5 hours. The resulting suspension is concentrated by evaporation under vacuum after cooling, and the residue is taken up with 300 ml of 2N hydrochloric acid. After removal of the precipitate by filtration, the filtrate is adjusted to pH 10 with conc. ammonia and extracted with 3×100 ml of dichloromethane. The combined organic phases are dried, filtered and concentrated by evaporation under vacuum. The oil obtained as residue crystallizes when stirred up with 30 ml of ethyl acetate.

Yield: 7.9 g (61%).
M.pt. 119°–121° C.
$C_{14}H_{19}N_3O_2$ (261.33).

$^1$H-NMR data (d$_6$-DMSO, TMS as internal standard): δ=1.0–1.2 (2 d) 3 H, 1.5–2.0 (m) 4 H, 2 H replaceable by D$_2$O, 2.1–3.5 (m) 3 H, 2.7 (t) 2 H, 4.1 (t) 2 H, 7.0–7.2 (dd) 2 H, 7.7–7.9 (dd) 2 H, 11.0 (broad) 1 H replaceable by D$_2$O.

EXAMPLE 5

6-[4-(3-aminopropyl)phenyl]-4,5-dihydro-5-methyl-3(2H)-pyridazinone

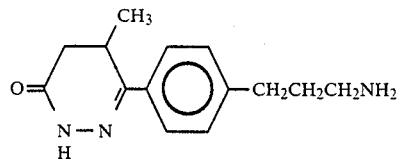

(a) 3-[4-(3-phthalimidopropyl)benzoyl]-butyric acid methyl ester.

8.2 g (50 mmol) of 3-methoxycarbonyl-2-methyl-propionic acid chloride and 13.3 g (50 mmol) of 3-phthalimidopropyl-benzene are reacted with 26 g of aluminum chloride in 1,2-dichloroethane analogously to Example 4(a). The oil obtained crystallizes from ethanol as beige coloured crystals.

Yield: 17.3 g (88%).
M.pt. 96°–97° C.
$C_{23}H_{23}NO_5$ (393.44).

(b)
6-[4-(3-aminopropyl)phenyl]-4,5-dihydro-5-methyl-3(2H)-pyridazinone.

9.3 g of a yellowish crude product is obtained analogously to Example 4(b) from 17.3 g (44 mmol) of 3-[4-(3-phthalimidopropyl)benzoyl]-butyric acid methyl ester and 11 ml (226 mmol) of hydrazine hydrate. This crude product is recrystallized from ethyl acetate.

Yield: 6.0 g (54%).
M.pt 115°–117° C.
$C_{14}H_{19}N_3O$ (245.32).

$^1$H-NMR data (d$_6$-DMSO, TMS as internal standard): δ=1.15 (d) 3 H, 1.4–2.0 (m) 4 H, 2 H replaceable by D$_2$O, 2.3–2.8 (m) 6 H, 2.9–3.3 (m) 1 H, 7.3–7.5 (m) 2 H, 7.7–7.9 (m) 2 H, 10.0 (broad) 1 H replaceable by D$_2$O ppm.

EXAMPLE 6

$N^1$-[4-(4-methyl-6-oxo-1,4,5,6-tetrahydropyridazin-3-yl) phenyl]-$N^2$-[3-(1H-imidazol-4-yl)propyl]-guanidine-hydriodide

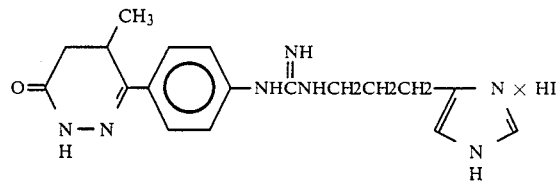

(a)
$N^1$-benzoyl-$N^2$-[4-(4-methyl-6-oxo-1,4,5,6-tetrahydropyridazin-3-yl)phenyl]-thiourea 4.85 g (29.7 mmol) of benzoyl isothiocyanate in 20 ml of dichloromethane are added dropwise at room temperature to a suspension of 6.00 g (29.5 mmol) of 6-(4-aminophenyl)-5-methyl-4,5-dihydro-3(2H)-pyridazinone in 70 ml of dichloromethane. After further stirring for 1 hour at room temperature, the precipitate formed in suction filtered and washed with 20 ml of dichloromethane. 10.21 g (94%) of pale yellow crystals are obtained.

M.pt 235°–237° C. $C_{19}H_{18}N_4O_2S$ (366.44).

(b)
N-[4-(4-methyl-6-oxo-1,4,5,6-tetrahydropyridazin-3-yl)-phenyl]-thiourea.

10.17 g (27.8 mmol) of $N^1$-benzoyl-$N^2$-[4-(4-methyl-6-oxo-1,4,5,6-tetrahydropyridazin-3-yl)phenyl]-thiourea are boiled up with 7.6 g (55 mmol) of potassium carbonate in 300 ml of methanol and 95 ml of water for 1 hour. After cooling to room temperature and stirring, the resulting crystals are suction filtered, washed with 20 ml of methanol and dried under vacuum.

Yield: 6.4 g (88%).
Colourless crystals, m.pt. 233°–234° C.
$C_{12}H_{14}N_4OS$ (262.33).

(c)
N-[4-(4-methyl-6-oxo-1,4,5,6-tetrahydropyridazin-3-yl)-phenyl]-S-methyl-isothiuronium iodide.

6.4 g (24.4 mmol) of N-[4-(4-methyl-6-oxo-1,4,5,6-tetrahydropyridazin-3-yl)phenyl]-thiourea are suspended in 150 ml of ethanol. 2.0 ml (32 mmol) of methyl iodide are added and after 20 hours stirring at room temperature the unreacted starting compound is suction filtered and the mother liquor is by concentrated by evaporation under vacuum. The solid residue is recrystallized from ethanol/methanol (4:1).

Yield: 2.1 g (21%).
Colourless crystals melting at 210° C.
$C_{13}H_{17}IN_4OS$ (404.26).

(d)
$N^1$-[4-(4-methyl-6-oxo-1,4,5,6-tetrahydropyridazin-3-yl)-phenyl]-$N^2$-[3-(1H-imidazol-4-yl)propyl]-guanidine hydriodide.

1.00 g (2.47 mmol) of N-[4-(4-methyl-6-oxo-1,4,5,6-tetrahydropyridazin-3-yl)phenyl]-S-methyl-isothiuroniumiodide and 0.31 g (2.5 mmol) of 3-(1H-imidazol-4-yl)propylamine in 50 ml of acetonitrile are boiled under a nitrogen atomosphere for 3 hours. After removal of the solvent by evaporation under vacuum, the oil obtained is chromatographically purified on silica gel with dichloromethane/methanol (90:10→80:20→50:50) as solvent. The polar main fraction yields 0.73 g (61%) of a colourless, amorphous solid after evaporation under vacuum.

$C_{18}H_{24}IN_7O$ (481.33).

$^1$H-NMR data (d$_6$-DMSO, TMS as internal standard): δ=1.1 (d) 3 H, 1.8 (quin) 2 H, 2.1–2.9 (m) 4 H, 3.2–3.6 (m) 3 H, 6.9 (s) 1 H, 7.3 (d) 2 H, 7.6 (s) 1 H, 7.9 (d) 2 H ppm.

EXAMPLE 7

$N^1$-[3-[N-[4-(4-methyl-6-oxo-1,4,5,6-tetrahydropyridazin-3-yl)phenyl]carboxamido]propyl]-$N^2$-[3-(1H-imidazol-4-yl)propyl]-guanidine

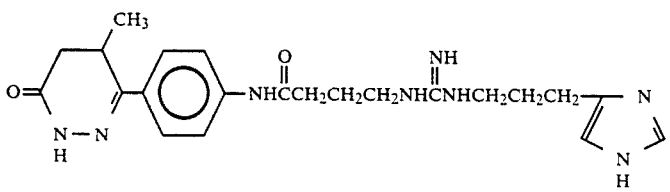

(a) $N^1$-benzoyl-$N^2$-[3-[N-[4-(4-methyl-6-oxo-1,4,5,6-tetrahydropyridazin-3-yl)phenyl]carboxamido]propyl]-thiourea.

3.4 g (20.8 mmol) of benzoyl isothiocyanate in 20 ml of ethyl acetate are added dropwise over a period of 15 minutes to a suspension of 6.0 g (20.8 mmol) of 4-amino-N-[4-(4-methyl-6-oxo-1,4,5,6-tetrahydropyridazin-3-yl)phenyl]-butyramide in 100 ml of acetonitrile. After 1 hour's stirring at room temperature, the clear solution is concentrated by evaporation under vacuum and the residue is stirred up with a mixture of 200 ml of methanol and 50 ml of water. 3.7 g (40%) of a colourless solid crystallize.

M.pt 190°–192° C.
$C_{23}H_{25}N_5O_3S$ (451.54).

(b) N-[3-[N-[4-(4-methyl-6-oxo-1,4,5,6-tetrahydropyridazin3-yl)phenyl](carboxamido]propyl]-thiourea.

Prepared by a method analogous to that of Example 6(b) from 3.70 g (8.2 mmol) of $N^1$-benzoyl-$N^2$-[3-[N-[4-(4-methyl-6-oxo-1,4,5,6-tetrahydropyridazin-3-yl)phenyl]carboxamido]propyl]-thiourea and 2.26 g (16.4 mmol) of potassium carbonate.

Yield: 2.69 g (95%).
Colourless crystals, melting point 142°–144° C.
$C_{16}H_{21}N_5O_2S$ (347.44).

(c) N-[3-[N-[4-(4-methyl-6-oxo-1,4,5,6-tetrahydropyridazin3-yl)phenyl]carboxamido]propyl]-S-methyl-isothiuronium iodide.

1.20 g (3.5 mmol) of N-[3-[N-[4-(4-methyl-6-oxo-1,4,5,6-tetrahydropyridazin-3-yl)phenyl]carboxamido]-propyl]-thiourea and 0.30 ml (4.8 mmol) of methyl iodide in 100 ml of ethanol are stirred at room temperature for 4 days. The resulting solid is suction filtered, washed with ethanol and dried under vacuum.

Yield: 1.06 g (63%).
Colourless crystals, M.pt. 214°–216° C.
$C_{17}H_{24}IN_5O_2S$ (489.37).

(d) $N^1$-[3-[N-[4-(4-methyl-6-oxo-1,4,5,6-tetrahydropyridazin-3-yl)phenyl]carboxamido]propyl]-$N^2$-[3-(1H-imidazol-4-yl)propyl]-guanidine.

1.00 g (2.04 mmol) of N-[3-[N-[4-(4-methyl-6-oxo-1,4,5,6-tetrahydropyridazin-3-yl)phenyl]carboxamido]-propyl]-S-methylisothiuronium iodide and 0.26 g (2.06 mmol) of 3-(1H-imidazol-4-yl)-propylamine are boiled in 40 ml of acetonitrile for 4 hours. Resinous impurities are removed by decanting the solution while still hot and the solution is then concentrated by evaporation under vacuum. The residue is chromatographed on silica gel using a mixture of ethyl acetate, methanol and concentrated ammonia saturated with ammonium chloride (50:48:2) as solvent. The polar main fraction is concentrated by evaporation under vacuum and the residue is taken up with 10 ml of saturated potassium carbonate solution and extracted with 2×20 ml of isopropanol. The organic phase is dehydrated with potassium carbonate, filtered and evaporated to dryness under vacuum. 0.31 g (35%) of a colourless, amorphous solid is obtained as residue.

$C_{22}H_{30}N_8O_2$ (438.53).

$^1$H-NMR data (CD$_3$OD, TMS as internal standard): δ=1.15 (d) 3 H, 1.7–2.1 (m) 4 H, 2.3–2.8 (m) 6 H, 3.1–3.5 (m) 5 H, 5.0 (broad) 6 H replaceable by D$_2$O, 6.9 (s) 1 H, 7.7 (s) 1 H, 7.7–8.0 (m) 4 H ppm.

EXAMPLE 8

$N^1$-[3-[N-[4-(4-methyl-6-oxo-1,4,5,6-tetrahydropyridazin3-yl)phenyl]amino]propyl]-$N^2$-[3-(1H-imidazol-4-yl)propyl]guanidine dihydrobromide

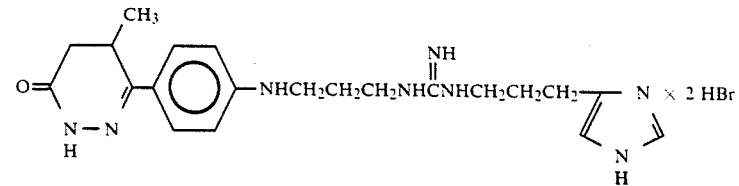

0.37 g (1.4 mmol) of 6-[4-(3-aminopropylamino)-phenyl]-4,5dihydro-5-methyl-3(2H)-pyridazinone and 0.51 g (1.4 mmol) of N-[3-(1H-imidazol-4-yl)propyl]-S-methyl-isothiuronium dihydrobromide are boiled under reflux in 30 ml of acetonitrile and 2 ml of pyridine for 5 hours. The solution is evaporated to dryness under vacuum and the residue is stirred up with 20 ml of ethanol. Unreacted isothiuronium salt is filtered off and the filtrate is concentrated by evaporation under vacuum. The crude product is chromatographed on silica gel with ethyl acetate/ethanol/conc. ammonia (15:10:2). The main fraction yields 0.16 g (36%) of a yellowish amorphous solid after removal of the solvent by evaporation under vacuum.

$C_{21}H_{32}Br_2N_8O$ (572.36).

$^1$H-NMR data (CD$_3$OD, TMS as internal standard): δ = 1.15 (d) 3 H, 1.8–2.2 (m) 4 H, 2.2–3.5 (m) 11 H, 4.9 (broad) 8 H, replaceable by D$_2$O, 6.7–6.9 (m) 2 H, 7.5 (s) 1 H, 7.7–7.9 (m) 2 H, 8.9 (d) 1 H ppm.

EXAMPLE 9

N$^1$-[3-[1-[4-(6-oxo-1,4,5,6-tetrahydropyridazin-3-yl)phenyl] imidazol-4-yl]propyl]-N$^2$-[3-(1H-imidazol-4-yl)propyl]-guanidine 0.30 g (1.00 mmol) of 6-[4-[4-(3-aminopropyl)-1H-imidazol-1-yl]phenyl]-4,5-dihydro-3(2H)-pyridazinone and 0.37 g (1.02 mmol) of N-[3-(1H-imidazol-4-yl)propyl]-S-methyl-isothiuronium dihydrobromide are boiled in 30 ml of pyridine for 16 hours under a nitrogen atmosphere. The residue obtained after evaporation of the solution under vacuum is chromatographically purified on silica gel using a mixture of ethyl acetate, methanol and conc. ammonia saturated with ammonium chloride (50:48:2) as solvent.

The main fraction is concentrated by evaporation under vacuum, taken up with 10 ml of saturated potassium carbonate and extracted with 2×20 ml of isopropanol. After drying and evaporation under vacuum, the organic phase yields the title compound as a colourless, amorphous solid.

Yield: 0.19 g (42%).

$C_{23}H_{29}N_9O$ (447.54).

$^1$H-NMR data (CD$_3$OD, TMS as internal standard): δ = 1.8–2.2 (m) 4 H, 2.5–3.4 (m) 12 H, 5.0 (broad) 5 H replaceable by D$_2$O, 6.9 (s) 1 H, 7.5–8.3 (m) 7 H ppm.

EXAMPLE 10

N$^1$-[3-[4-methyl-6-oxo-1,4,5,6-tetrahydropyridazin-3-yl) phenoxy]propyl]-N$^2$-[3-(1H-imidazol-4-yl)propyl]-guanidine (a)

N$^1$-benzoyl-N$^2$-[3-[4-(4-methyl-6-oxo-1,4,5,6-tetrahydropyridazin-3-yl)phenoxy]propyl]-thiourea 6.55 g (40 mmol) of benzoyl isothiocyanate in 20 ml of dichloromethane are added dropwise over a period of 20 minutes to a suspension of 10.45 g (40 mmol) of 6-[4-(3-aminopropoxy) phenyl]-4,5-dihydro-5-methyl-3(2H)-pyridazinone in 100 ml of dichloromethane.

The solution is then stirred for 30 minutes and concentrated by evaporation under vacuum and the residue is crystallized by stirring it up with 30 ml of acetonitrile.

Yield: 11.38 g (67%).

M.pt. 172°–176° C.

$C_{22}H_{24}N_4O_3S$ (424.52).

(b)

N-[3-[4-(4-methyl-6-oxo-1,4,5,6-tetrahydropyridazin-3-yl)phenoxy]propyl]-thiourea.

Obtained by a method analogous to that in Example 6(b) from 8.0 g (18.8 mmol) of N$^1$-benzoyl-N$^2$-[3-[4-(4-methyl-6-oxo-1,4,5,6-tetrahydropyridazin-3-yl)phenoxy]propyl]-thiourea and 5.2 g (38 mmol) of potassium carbonate.

Yield: 5.3 g (88%).

Colourless crystals, m.pt. 196°–198° C.

$C_{15}H_{20}N_4O_2S$ (320.41).

(c)

N-[3-[4-(4-methyl-6-oxo-1,4,5,6-tetrahydropyridazin-3-yl)phenoxy]propyl]-S-methyl-isothiuronium iodide.

Prepared by a method analogous to that of Example 7(c) from 3.7 g (11.5 mmol) of N-[3-[4-(4-methyl-6-oxo-1,4,5,6-tetrahydropyridazin-3-yl)phenoxy]propyl]-thiourea and 0.80 ml (12 mmol) of methyl iodide. 3.4 g (67%) of a yellowish, amorphous solid are obtained.

$C_{16}H_{23}IN_4O_2S$ (462.34).

(d)
N¹-[3-[4-(4-methyl-6-oxo-1,4,5,6-tetrahydropyridazin-3-yl)phenoxy]propyl]-N²-[3-(1H-imidazol-4-yl)propyl]-guanidine.

0.24 g (27%) of a yellowish, amorphous solid is obtained from 1.00 g (2.2 mmol) of N-[3-[4-(4-methyl-6-oxo-1,4,5,6-tetrahydropyridazin-3-yl)phenoxy]propyl]-S-methyl-isothiuronium iodide and 0.30 g (2.4 mmol) of 3-(1H-imidazol-4-yl)-propylamine by a method analogous to that of Example 7 (d).

$C_{21}H_{29}N_7O_2$ (411.51). ¹H-NMR data (CD₃OD, TMS as internal standard): δ=1.0–1.3 (2d) 3 H, 1.7–2.2 (m) 4 H, 2.5–2.8 (m) 4 H, 3.0–3.5 (m) 5 H, 4.2 (t) 2 H, 5.0 (broad) 5 H replaceable by D₂O, 6.9 (s) 1 H, 7.0–7.2 (m) 2 H, 7.7 (s) 1 H, 7.8–8.0 (m) 2 H ppm.

EXAMPLE 11

N¹-[3-[4-(4-methyl-6-oxo-1,4,5,6-tetrahydropyridazin-3-yl)phenyl]propyl]-N²-[3-(1H-imidazol-4-yl)propyl]-guanidine

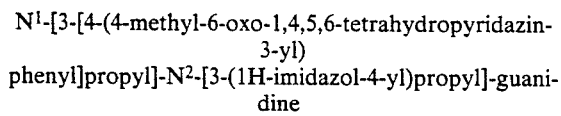

0.44 g (51%) of an amorphous, solidified foam is obtained by a method analogous to that of Example 7(d) from 1.00 g (2.2 mmol) of N-[3-[4-(4-methyl-6-oxo-1,4,5,6-tetrahydropyridazin-3-yl)phenyl]propyl]-S-methyl-isothiuronium iodide and 0.28 g (2.2 mmol) of 3-(1H-imidazol-4-yl)-propylamine.

$C_{21}H_{29}N_7O$ (395.50).

¹H-NMR data (CD₃OD, TMS as internal standard): δ=1.0–1.3 (2d) 3 H, 1.7–2.1 (m) 4 H, 2.5–2.9 (m) 6 H, 3.0–3.4 (m) 5 H, 5.0 (broad) 5 H replaceable by D₂O, 6.9 (s) 1 H, 7.3–8.0 (m) 5 H ppm,

We claim:

1. Dihydropyridazinone derivatives corresponding to formula I

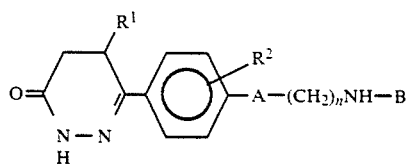 (I)

wherein R¹ denotes a hydrogen atom or a straight chained or branched C₁ to C₄ alkyl group, R² denotes a hydrogen atom, a straight chained or branched C₁ to C₄ alkyl group, a C₁ to C₄ alkoxy group, a halogen atom, a nitro group or an amino group, A denotes an oxygen atom, the group NH or

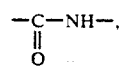

an imidazole ring attached to positions 1 and 4 or a single bond, and B denotes a group of the formula

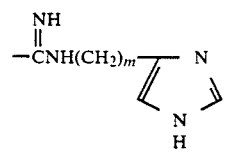

2. Dihydropyridazinone derivatives according to claim 1, wherein R¹ denotes a hydrogen atom or a straight chained or branched C₁ to C₄ alkyl group, R² denotes a hydrogen atom, a straight chained or branched C₁ to C₄ alkyl group, a C₁ to C₄ alkoxy group, a halogen atom, a nitro group or an amino group, A denotes an oxygen atom, the group NH or

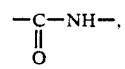

an imidazole ring attached in positions 1 and 4 or a single bond and B stands for a group of the formula

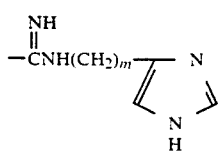

wherein m has the value 2 or 3 and n denotes an integer with a value from 0 to 6.

3. Dihydropyridazinone derivatives according to claim 1, wherein R¹ denotes a hydrogen atom or a straight chained or branched C₁ to C₄ alkyl group, in particular a methyl group, R² denotes a hydrogen atom, A denotes an oxygen atom, the group NH or

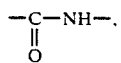

an imidazole ring attached in positions 1 and 4 or a single bond, and B denotes a group of the formula

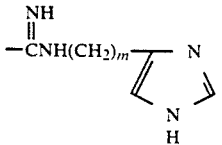

wherein m has the value 2 or 3, in particular 3, and n denotes an integer with a value from 0 to 6.

4. N¹-[3-[N-[4-(4-methyl-6-oxo-1,4,5,6-tetrahydropyridazin3-yl)-phenyl]-carboxamido]propyl]-N²-[3-(1H-imidazol-4-yl) propyl]-guanidine.

5. $N^1$-[4-(4-methyl-6-oxo-1,4,5,6-tetrahydropyridazin-3-yl) phenyl]-$N^2$-[3-(1H-imidazol-4-yl)propyl]-guanidine.

6. A composition for use as a pharmaceutical preparation, comprising a compound according to claim 1 together with at least on inert, pharmaceutically acceptable carrier or diluent.

7. A method for eliciting a positive inotropic response in a mammalian organism in need of such treatment, comprising administering to such organism a positive inotropically effective amount of a dihydropyridazinone as defined in claim 1, or a physiologically effective salt thereof.

8. A method according to claim 7, wherein said method includes administration of said dihydropyridazinone compound in oral dosage form.

9. A method according to claim 7, wherein said method includes buccal administration of said dihydropyridazinone compound.

10. A method according to claim 7, wherein said method includes topical administration of said dihydropyridazinone compound.

11. A method according to claim 7, wherein said method includes parenteral administration of said dihydropyridazinone compound.

12. A method according to claim 7, wherein said method includes rectal administration of said dihydropyridazinone compound.

13. A method for treating heart disease in a mammalian organism in need of such treatment, comprising administering to such organism a therapeutically effective amount of a dihydropyridazinone compound as defined in claim 1 or a physiologically effective salt thereof.

* * * * *